United States Patent
Uttley et al.

(10) Patent No.: US 9,298,885 B2
(45) Date of Patent: Mar. 29, 2016

(54) MEDICAL CART SYSTEM

(71) Applicant: Huntingdon Telemed, LLC, Bonita Springs, FL (US)

(72) Inventors: Thomas Uttley, Naples, FL (US); David Boll, Avon, OH (US); Maynard Payumo, Parma, OH (US); William Rabbitt, Chesterland, OH (US); James Szpak, Cleveland Heights, OH (US); Jason Tilk, Cleveland Heights, OH (US); Robert Vystrcil, Garrettsville, OH (US)

(73) Assignee: HUNTINGDON TELEMED, LLC, Bonita Springs, FL (US)

( * ) Notice: Subject to any disclaimer, the term of this patent is extended or adjusted under 35 U.S.C. 154(b) by 0 days.

(21) Appl. No.: 14/920,151

(22) Filed: Oct. 22, 2015

(65) Prior Publication Data

US 2016/0042139 A1 Feb. 11, 2016

Related U.S. Application Data

(63) Continuation of application No. 14/255,556, filed on Apr. 17, 2014, now Pat. No. 9,179,493.

(51) Int. Cl.
  *B62B 1/00* (2006.01)
  *G06F 19/00* (2011.01)
  *B62B 1/26* (2006.01)
  (Continued)

(52) U.S. Cl.
  CPC .............. *G06F 19/3418* (2013.01); *B62B 1/12* (2013.01); *B62B 1/26* (2013.01); *G06F 1/1605* (2013.01)

(58) Field of Classification Search
  CPC ............ B62B 1/12; B62B 1/125; B62B 3/02; B62B 3/10; B62B 5/0083; B62B 2202/404; B62B 2202/406; B62B 1/262
  See application file for complete search history.

(56) References Cited

U.S. PATENT DOCUMENTS

| 5,924,988 | A | 7/1999 | Burris et al. |
| 7,518,508 | B2 | 4/2009 | Cvek |
| 8,172,242 | B1 * | 5/2012 | Crandall .............. A61B 5/0059 280/47.35 |

(Continued)

OTHER PUBLICATIONS

Esteban Martin Kloosterman, et al., "Real-Time Remote Interrogation and Guided Reprogramming of Cardiac Implantable Electronic Devices." The Journal of Innovations in Cardiac Rhythm Management, vol. 4, pp. 1320-1324, Jul. 2013.

(Continued)

*Primary Examiner* — John Walters
*Assistant Examiner* — James Triggs
(74) *Attorney, Agent, or Firm* — Renner, Otto, Boisselle & Sklar, LLP

(57) ABSTRACT

A medical cart includes an interface assembly including a display, a speaker, a camera and a microphone. The interface assembly is operatively connected to an enclosure at a connecting portion that is operable to reposition the interface assembly from a transporting configuration in which the interface assembly is disposed inside the enclosure to a deployed configuration in which the interface assembly is disposed outside of the enclosure. The medical cart also includes a set of wheels operably connected to at least one of the enclosure or a pivoting assembly operable to pivot from the transporting configuration in which only the set of wheels makes contact with a transporting surface to the deployed configuration in which a portion of the cart in addition to the set of wheels makes contact with the transporting surface for stabilizing the cart in the deployed configuration.

3 Claims, 13 Drawing Sheets

(51) Int. Cl.
    *B62B 1/12*    (2006.01)
    *G06F 1/16*    (2006.01)

(56) References Cited

U.S. PATENT DOCUMENTS

| | | | |
|---|---|---|---|
| 8,286,977 B2 | 10/2012 | Butler et al. | |
| 8,526,176 B2 * | 9/2013 | Clark | A61B 5/0002 248/918 |
| 8,534,779 B2 | 9/2013 | Schaaf | |
| 8,662,605 B2 | 3/2014 | McRorie et al. | |
| 2005/0288571 A1 | 12/2005 | Perkins et al. | |
| 2008/0185945 A1 | 8/2008 | Low | |
| 2012/0212116 A1 | 8/2012 | McRorie et al. | |

OTHER PUBLICATIONS

"First Exam, Mobile Telemedicine Station", GlobalMed, www.globalmed.com, 4 pages, 2013.

"Mobile Telemedicine Station", GlobalMed, www.globalmed.com, 2 pages, 2012.

"Transportation Exam Station", GlobalMed, www.globalmed.com, 2 pages, 2013.

* cited by examiner

MEDICAL CART SYSTEM

FIELD OF THE INVENTION

The present disclosure relates generally to remote medical care and particularly to a medical cart system.

BACKGROUND

In some cases, access to medical care for certain specialties such as, for example, psychological care may not be widely available particularly in rural areas or even urban areas that are significantly spread out. In other cases, care may be available, but the cost of providing individualized care may be prohibitive to patients and/or insurance programs.

Remote care systems have been proposed in which a doctor or other medical practitioner may provide some level of care from a location remote to the patient. In prior art systems, however, the doctor/patient interaction facilitated by the systems may be less than optimal. Remote care systems should allow the patient to experience interaction with the doctor that is as similar as possible to the interaction that the patient would have experienced if the patient and the doctor were in the same room. Conventional remote care systems do not provide that.

Moreover, because of their construction, weight, power structure, etc., prior art remote care systems were effectively bound to a single medical facility and were not effectively and easily transported from one facility to another facility. The cost of remote care systems that are effectively bound to a single medical facility may be prohibitive because multiple systems would be needed to service multiple facilities, which increases costs and reduces availability of care.

SUMMARY OF THE INVENTION

This disclosure provides a medical cart that provides for doctor/patient interaction that is similar to the interaction that the patient would have experienced if the patient and the doctor were in the same location. Moreover, the medical cart of the present disclosure provides for doctor/patient interaction that is facilitated by a third person, a facilitator, who may monitor various aspects of the communication between doctor and patient to ensure a satisfactory experience for the patient. The medical cart of the present disclosure also gives the patient the opportunity to experience interaction with the doctor without the facilitator becoming a distraction.

The medical cart of the present disclosure may be easily and efficiently transported, not only within a facility, but also from one facility to another because the cart is relatively light in weight, particularly as compared to prior art medical carts currently used in hospitals and other facilities. Moreover, the cart is reconfigurable to make it easily deployable, storable and transportable. Ease of transportation may allow for a single doctor or medical practitioner utilizing a single medical cart to provide consultation and/or care to multiple patients at multiple facilities potentially expanding availability of care and/or reducing costs.

These and further features of the present invention will be described with reference to the attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the terms of the appended claims.

BRIEF DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1A:
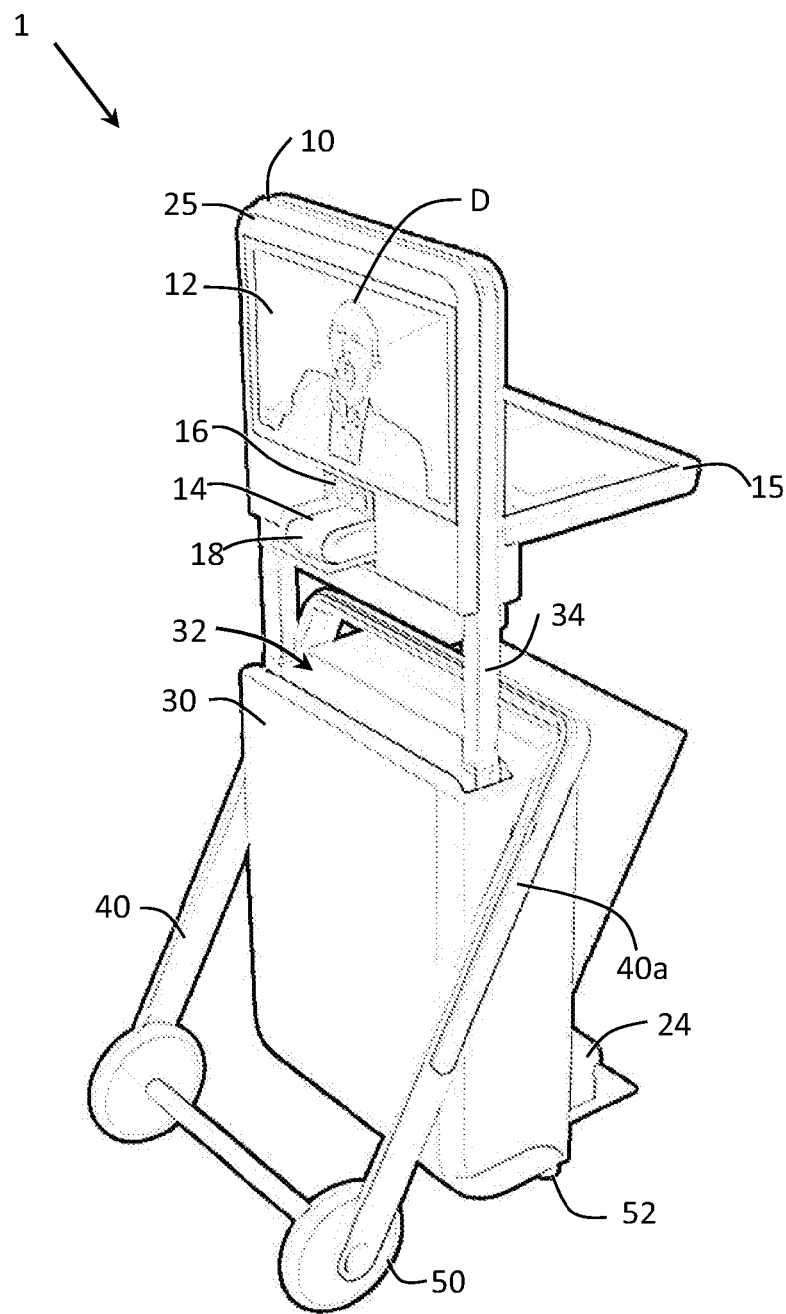
FIGS. 1A and 1B illustrate an exemplary medical cart.
Figure 1B:
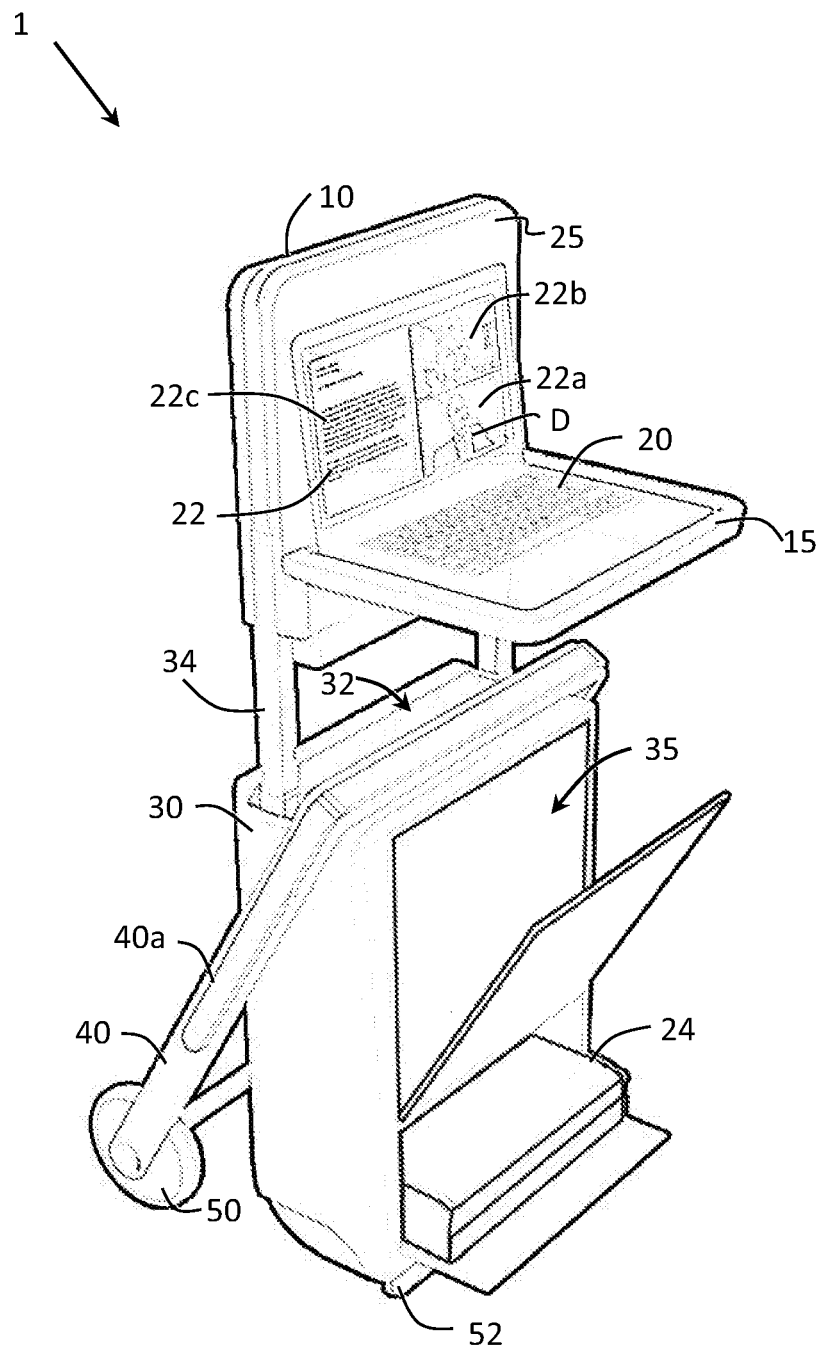

FIGS. 1A and 1B illustrate an exemplary medical cart 1. FIG. 1A illustrates the exemplary medical cart 1 from the perspective of a patient while FIG. 1B illustrates the cart 1 from the perspective of a facilitator as described below.

The medical cart 1 includes an interface assembly 10.

On the patient side (FIG. 1A), the interface assembly 10 includes a patient-side display 12, a speaker 14, a camera 16 and a microphone 18. The cart 1 is also equipped with a communication module as further disclosed below that receives video and audio communication from a location remote to the location of the cart 1. The communication module displays the received video on the display 12 and plays the received audio through the speaker 14. The communication module also receives a video image from the camera 16 and sound from the microphone 18, and transmits the received video image and sound to the remote location. The communication module may be implemented as a node in a wired or wireless communication network.

The video and audio communication received from the remote location may be, for example, a transmission from a doctor D or other medical practitioner. A camera and microphone may be set up at the remote location to allow the doctor or medical practitioner to communicate with a patient facing the display 12 and within audible range of the speaker 14. The camera 16 and the microphone 18 may capture the patient's likeness and voice and allow the patient to communicate with the doctor D or medical practitioner.

For example, the cart 1 may be deployed at a medical facility (e.g., hospital, nursing home, psychiatric care facility, etc.) such that a patient may interact with a doctor D via the interface assembly 10. The doctor D or medical practitioner may be at a remote facility. By communicating via the cart 1 the doctor D may provide consultation and care to the patient remotely. Thus, the cart 1 may improve the availability and/or cost of medical care to, for example, remote areas in which specific medical care may not be readily available. The cart 1 may also allow a single doctor or medical practitioner to provide consultation and/or care to multiple patients at multiple facilities potentially expanding availability of care and/or reducing costs.

The cart 1 may be deployed with the assistance of a facilitator, a person that would attend to transport and setup of the cart 1. The facilitator may also attend to any technical issues or concerns regarding the cart 1, to completion of medical forms, and may generally monitor the interaction between doctor and patient to ensure a satisfactory experience for the patient.

On the facilitator side (FIG. 1B), the cart 1 includes a tray 15 and a computer 20 that includes a facilitator-side display 22. For purposes of illustration the computer 20 is shown as a laptop computer resting on the tray 15. In one embodiment, the computer 20 may be a tablet computer connected to the tray 15 or to a different portion of the interface assembly 10 or the cart 1. In another embodiment, the computer 20 may be a desktop or tower type computer with the main CPU portion of the computer 20 located on the tray 15, the interface assembly 10 or in another portion of the cart 1, while the display 22 may be located on the tray 15 or a different portion of the interface assembly 10 or the cart 1. In one embodiment, the tray 15 is less than a full tray, but instead may be a skeleton or frame to which the computer 20 or the display 22 may attach or on which they may rest.

The cart 1 may also be equipped with a facilitator module as further disclosed below that receives the video and audio communication from the remote location similar to the communication module described above. The facilitator module displays the received video on the display 22. The facilitator module may also play the received audio through speakers (not shown) such as, for example, headphones that the facilitator may wear. The facilitator module displays the received video and may play the received audio such that the facilitator may monitor communication between doctor and patient. In the illustrated embodiment, the facilitator module displays the received video corresponding to the transmission from the doctor D on a first portion 22a of the facilitator-side display 22.

In one embodiment, the facilitator module may also receive the video image from the camera 16 and sound from the microphone 18 similar to the communication module described above. The facilitator module displays the video image from the camera 16 on the display 22. The facilitator module may also play the sound from the microphone 18 through speakers (not shown) such as, for example, headphones that the facilitator may wear. The facilitator module displays the video image from the camera 16 and may play the sound from the microphone 18 such that the facilitator may monitor communication between doctor and patient. In the illustrated embodiment, the facilitator module displays the video image from the camera 16 on a second portion 22b of the facilitator-side display 22.

In another embodiment, the facilitator module may also receive data corresponding to medical forms (e.g., patient's medical records, medical charts, health history, insurance forms, Medicare forms, prescriptions, etc.) relating to the doctor D, to the patient, to the facility, etc. The facilitator module displays data corresponding to medical forms or the forms themselves on the second display 22 such that the facilitator may assist the doctor D or the patient in completing the medical forms. In the illustrated embodiment, the facilitator module displays data corresponding to medical forms on a third portion 22c of the second display 22. The cart 1 may further include a printer 24 that the facilitator may use to print any medical forms for the use of the patient, the doctor, the medical facility, etc.

Thus, cart 1 including the facilitator module may help the facilitator monitor various aspects of the communication between doctor and patient to, again, ensure a satisfactory experience for the patient.

In at least some cases, however, the doctor/patient interaction facilitated by the cart 1 may be disrupted by the presence of a third person, the facilitator. Ideally, the patient would be able to concentrate on the interaction with the doctor D via the display interface assembly 10 without the facilitator becoming a distraction.

To this end, the cart 1 may provide the first display 12 and the second display 22 at opposite ends of the cart 1. In the illustrated embodiment, the computer 20 is connected to or rests on the tray 15 such that the second display 22 faces in a direction opposite to the direction to which the first display 12 faces. In another embodiment, the second display 22 (not necessarily the computer 20) is connected to or rests on the tray 15 such that the second display 22 faces in a direction opposite to the direction to which the first display 12 faces. In yet another embodiment, the computer 20 and/or the display 22 are connected to portions of the cart 1 other than the tray 15 such that the second display 22 faces in a direction opposite to the direction to which the first display 12 faces. In yet another embodiment, the first display 12 and the second display 22 are disposed within the cart 1 such that the second display 22 faces in a direction different from, although not necessarily opposite to, the direction to which the first display 12 faces.

Moreover, in the illustrated embodiment, the cart 1 further includes a privacy screen 25 disposed between the first display 12 and the second display 22. The privacy screen 25 at least partially blocks a facilitator facing the display 22 from the view of the patient facing the first display 12. Thus, the facilitator, while facing the second display 22 and in a position on an opposite side of the cart 1 from a position in which a patient faces the first display 12, is at least partially blocked from view of the patient behind the privacy screen 25 when the patient is interacting with the doctor D.

Thus, in the arrangement of FIGS. 1A and 1B the cart 1 including the privacy screen 25 and/or having the first display 12 and second display 22 arranged so that they face in different directions may help preserve or enhance the doctor/patient interaction. This arrangement may effectively minimize any disruption created by the presence of the facilitator to the doctor/patient interaction. The patient would be more likely to concentrate on the interaction with the doctor D via the display interface assembly 10 without the facilitator becoming a distraction.

In one embodiment (not shown), the computer 20 is detachably connected to the tray 15 (or another portion of the cart 1) such that the facilitator may easily detach the computer 20 (or the display 22) from the cart 1. The computer 20 may form a wireless communication network with the interface assembly 10 or the cart 1 and communicate with the interface assembly 10 via the wireless communication network. For example, the cart 1 may include a first wireless communication interface and the computer 20 may include a second wireless communication interface wirelessly coupled to the first wireless communication interface. This arrangement may further minimize any disruption created by the presence of the facilitator to the doctor/patient interaction because the facilitator may be able to facilitate the doctor/patient interaction from a nearby yet remote location (e.g., a room near to the patient's room, outside of the door of the patient's room, etc.) This arrangement may help further preserve or enhance the doctor/patient interaction. The patient should be able to better experience the interaction with the doctor D via the display interface assembly 10 without the facilitator being a distraction.

Thus, the cart 1 may help ensure effective and satisfactory doctor/patient interaction.

Moreover, to reduce the cost and increase the availability of care, the cart 1 is not bound to a single medical facility. The cart 1 may be easily and efficiently transported, not only within a facility, but also from facility to facility. To this end, the cart 1 is relatively light in weight, particularly as compared to prior art medical carts currently used in hospitals and other facilities. Moreover, the cart 1 includes features that make it easily deployable, storable and transportable as described below.

FIGS. 2A-2F illustrate the exemplary cart 1 in various stages of deployment, store and transport.

Figure 2A:
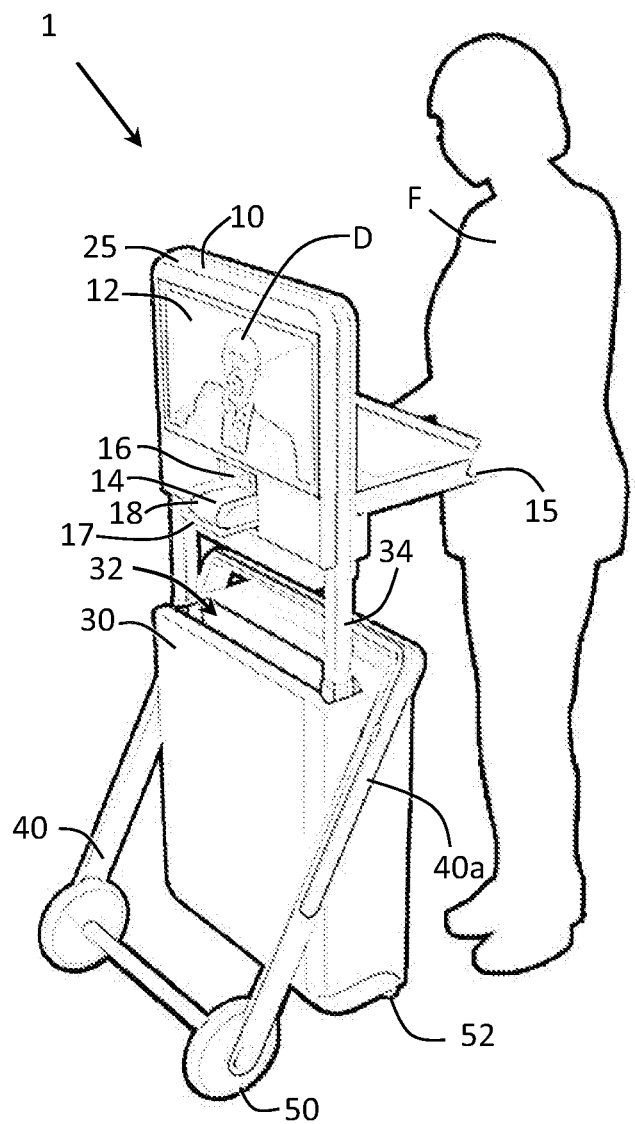
FIG. 2A illustrates the exemplary cart in a deployed configuration.

FIG. 2A illustrates the exemplary cart 1 in the deployed configuration, which is the same position illustrated in FIGS. 1A and 1B above. In the deployed configuration, a patient (not shown) may interact with a doctor D via the interface assembly 10 which includes the display 12, the speaker 14, the camera 16 and the microphone 18. Also, in the deployed configuration, a facilitator F may monitor various aspects of the communication between doctor and patient.

Figure 2B:
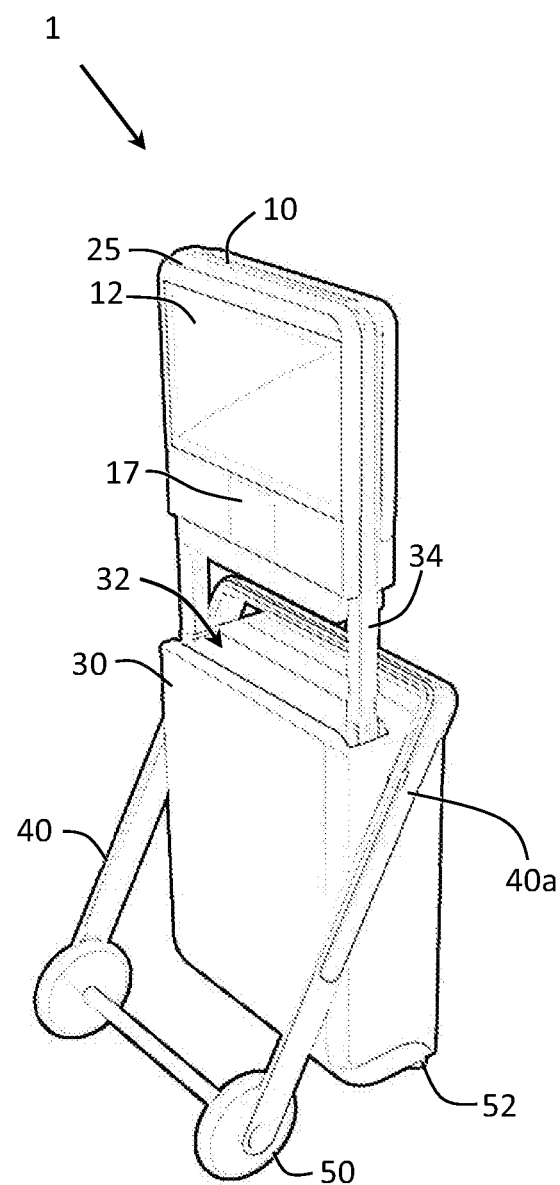
FIGS. 2B-2D illustrate the exemplary cart in configurations intermediary to deployment, store and transport.
Figure 2C:
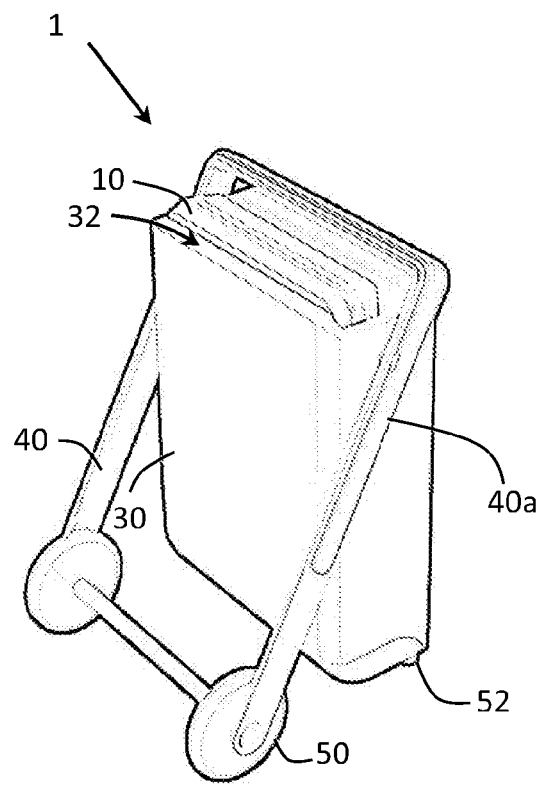
Figure 2D:
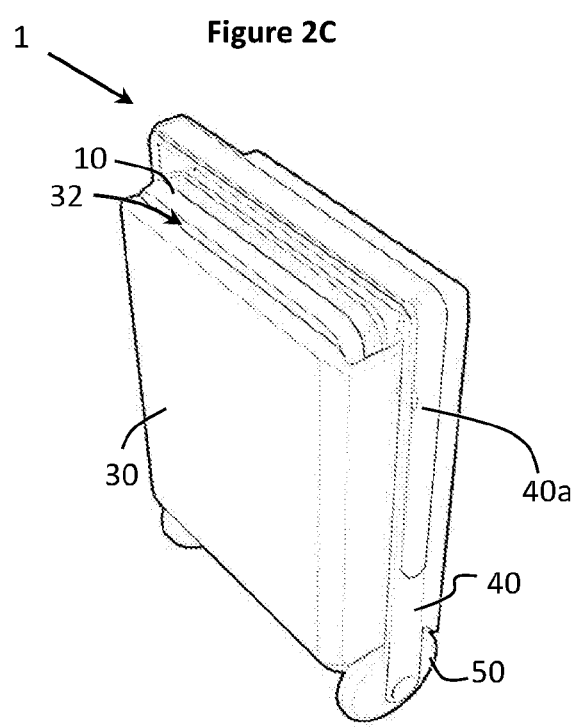
Figure 2E:
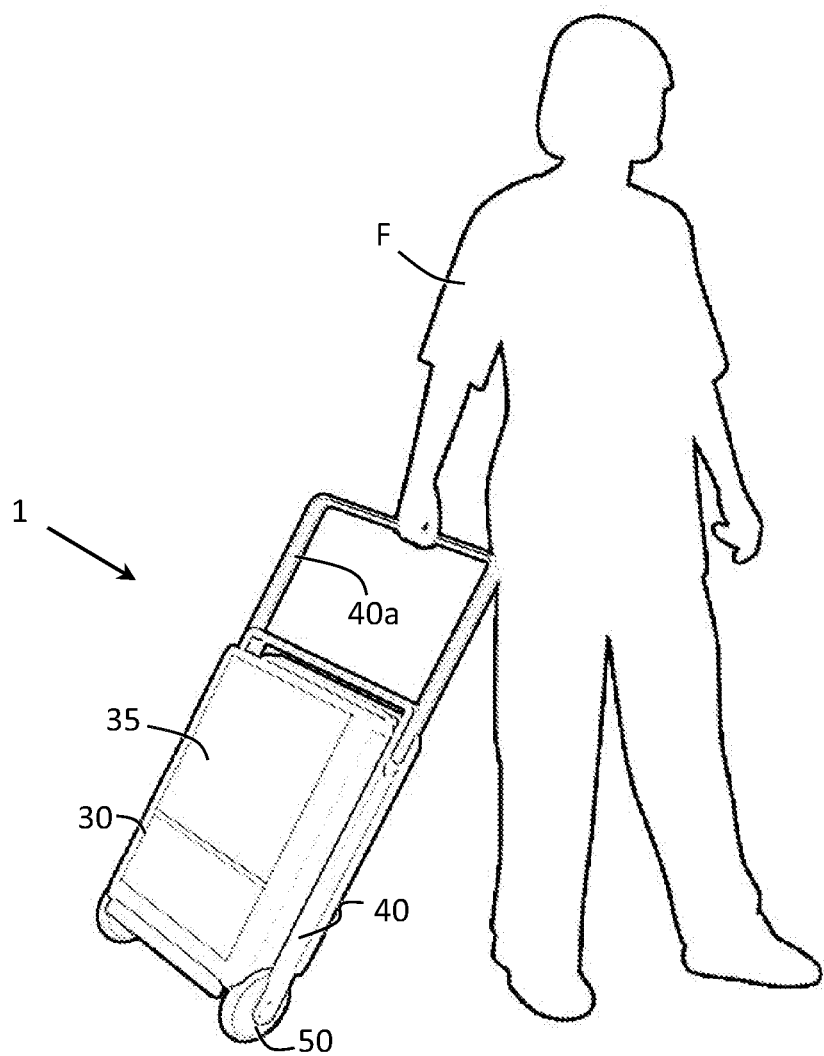
FIG. 2E illustrates the exemplary cart in a transporting configuration.
Figure 2F:
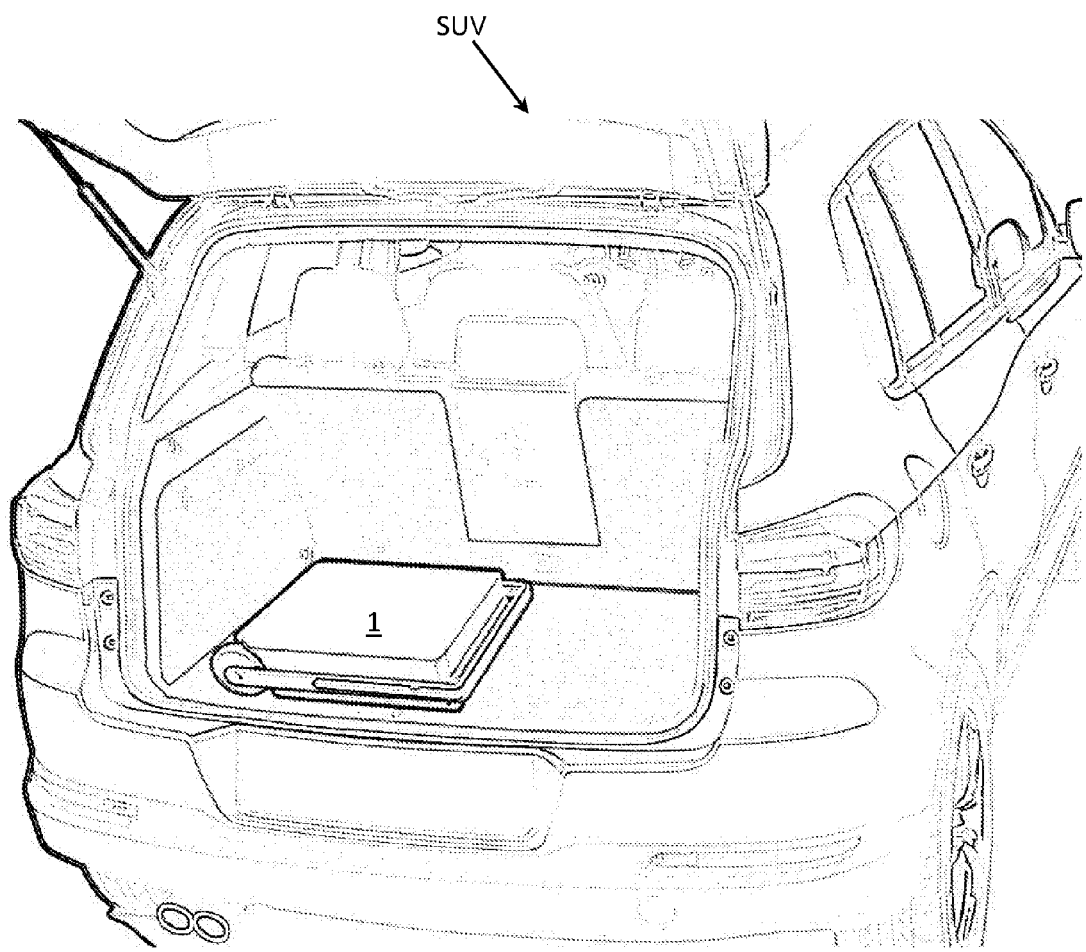
FIG. 2F illustrates the exemplary cart in a storing configuration.

FIG. 2E illustrates the exemplary cart 1 in the transporting configuration while FIG. 2F illustrates the cart 1 in the storing configuration. FIGS. 2B-2D illustrate the cart 1 in configurations intermediary between deployment, store and transport.

With return reference to FIG. 2A, the exemplary cart 1 includes a pivoting assembly 40 which, in the illustrated embodiment of FIG. 2C, is connected to the enclosure 30 so that it may pivot relative to the point of connection between the pivoting assembly 40 and the enclosure 30. In the illustrated embodiment, the cart 1 also includes a set of wheels 50 attached to the pivoting assembly 40. In other embodiments, the set of wheels may be connected to the enclosure 30 or to a portion of the cart 1 other than the pivoting assembly 40 or the enclosure 30. In the configurations of FIGS. 2A-2C, including the deployed configuration of FIG. 2A, another portion 52 of the cart 1 makes contact with the transporting surface (e.g. the floor of the medical facility, a sidewalk, etc.) in addition to the set of wheels 50. The wheels 50 in combination with the portion 52 form a multipoint base on which the cart 1 may stably rest in the deployed configuration.

The exemplary cart 1 also includes an enclosure 30. In the illustrated embodiment, the enclosure 30 has an opening 32 at one end and the interface assembly 10 includes a connecting portion 34 (e.g., slides, rails, etc.) that is operable to move (e.g., slide) the interface assembly 10 including the display 12, the speaker 14, the camera 16 and the microphone 18 so that it may be inserted into the enclosure 30 through the opening 32.

Inside the enclosure 30 the display 12, the speaker 14, the camera 16 and the microphone 18 may be protected from the environment including protection from contact, shock, moisture, dirt, etc. The enclosure 30 may be fabricated of metal, plastic or other suitable material that is durable and provide protection to the display 12, the speaker 14, the camera 16 and the microphone 18 when they are stored in the enclosure 30.

In the illustrated embodiment of FIG. 2A, prior to insertion of the interface assembly 10 into the enclosure 30, the tray 15 folds in towards the interface assembly 10 so that the tray 15 may be inserted into the enclosure 30 together with the interface assembly 10. Also, an assembly 17 that may hold or cover the speaker 14, the camera 16 and the microphone 18 may also fold in prior to insertion of the interface assembly 10 into the enclosure 30. The tray 15 and the assembly 17 may be connected to the interface assembly 10 by a hinge or similar element such that the facilitator F may fold the tray 15 and the assembly 17 towards the interface assembly 10.

FIG. 2B illustrates the exemplary cart 1 with the tray 15 and the assembly 17 folded toward the interface assembly 10. In one embodiment, the computer 20 may remain attached to the tray 15 while the tray 15 is folded towards the interface assembly 10. In another embodiment, the computer 20 may be detached from the tray 15 prior to folding of the tray 15 towards the interface assembly 10. The enclosure 30 may include a compartment 35 (see FIG. 1B) in which the computer 20 may be stored.

FIG. 2C illustrates the cart 1 after the interface assembly 10 including the display 12, the speaker 14, the camera 16 and the microphone 18 has been inserted into the enclosure 30 through the opening 32.

When reconfiguring the cart 1 from the deployed configuration to the transporting configuration, the pivoting assembly 40 may be pivoted about the point of connection between the pivoting assembly 40 and the enclosure 30 such that the pivoting assembly 40 is substantially parallel to the enclosure 30 and only the wheels 50 make contact with the transporting surface as shown in FIG. 2D. The pivoting assembly 40 includes a handle portion 40a that slides axially off the pivoting assembly 40 as shown in FIG. 2E to become a transporting handle for the cart 1. In the transporting configuration, as shown in FIG. 2E, the facilitator F may pull on the handle portion 40a to transport the cart 1 which rolls on the wheels 50.

Finally, the facilitator F may slide the handle portion 40a axially back into the pivoting portion 40 to minimize the profile of the cart 1 into the storing configuration as shown in FIG. 2F. In the storing configuration, the cart 1 may have a small enough profile to fit in the trunk of car or the back of an SUV as shown in FIG. 2F. The cart 1 is light enough for the facilitator F to be able to lift the cart 1 off the ground near the car or the SUV and place the cart 1 configured in the storing configuration in the trunk of the car or in the back of the SUV.

FIGS. 3A-3E illustrate a slightly different embodiment of the exemplary cart 1 in various stages of deployment, store and transport.

Figure 3A:
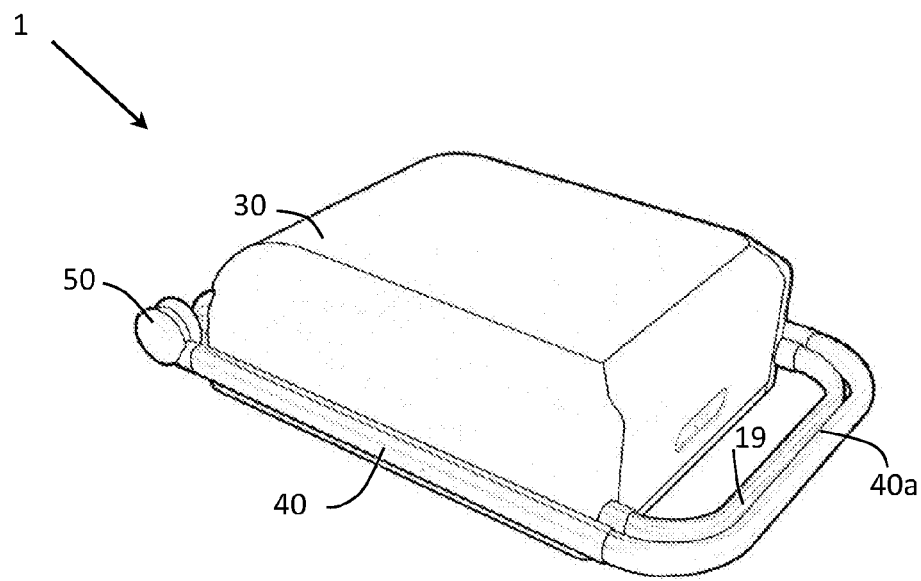
FIG. 3A illustrates an additional embodiment of the exemplary cart in the storing configuration.
Figure 3B:
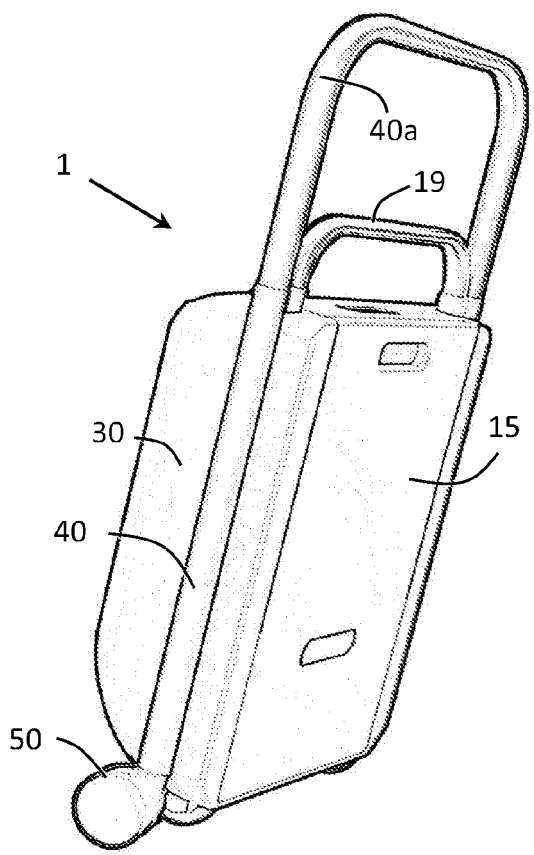
FIG. 3B illustrates the exemplary cart in the transporting configuration.

FIG. 3A illustrates the exemplary cart 1 in the storing configuration with its profile minimized for storage. FIG. 3B illustrates the exemplary cart 1 in the transporting configuration in which the handle portion 40a has been pulled axially off the pivoting portion 40 for transporting. By use of the handle portion 40a the facilitator F has also pulled up the cart 1 to a slanted stance for transportation. In the transporting configuration as shown in FIG. 3B, only the wheels 50 make contact with the transporting surface.

Figure 3C:
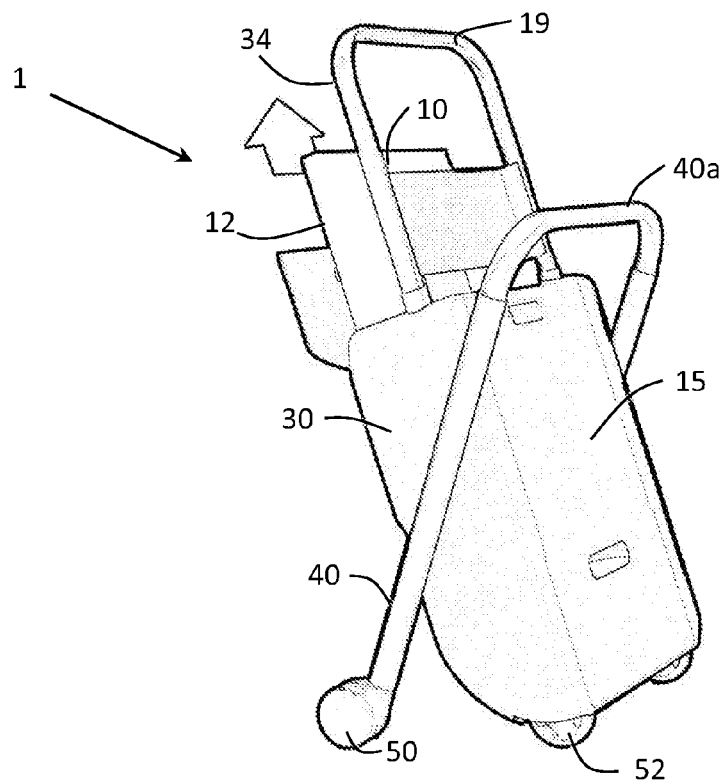
FIGS. 3C and 3D illustrate the exemplary cart in configurations intermediary to deployment, store and transport.

As shown in FIG. 3C, to reconfigure the cart 1 from the transporting configuration to the deployed configuration the handle portion 40a may slide axially back into the pivoting portion 40 and the pivoting assembly 40 may be pivoted about the point of connection between the pivoting assembly 40 and the enclosure 30 such that the wheels 50, which in the illustrated embodiment are connected to the pivoting assembly 40, are repositioned away from the enclosure 30. The wheels 50 in combination with the portion 52 form a multipoint base on which the cart 1 may stably rest in the deployed configuration. In the illustrated embodiment of FIGS. 3A-3E the portion 52 is embodied as a second set of wheels. In one embodiment, the first set of wheels 50 or the second set of wheels 52 or both include a locking mechanism to prevent the wheels 50 and/or 52 from rotating when the cart 1 is in the deployed configuration.

Figure 3D:
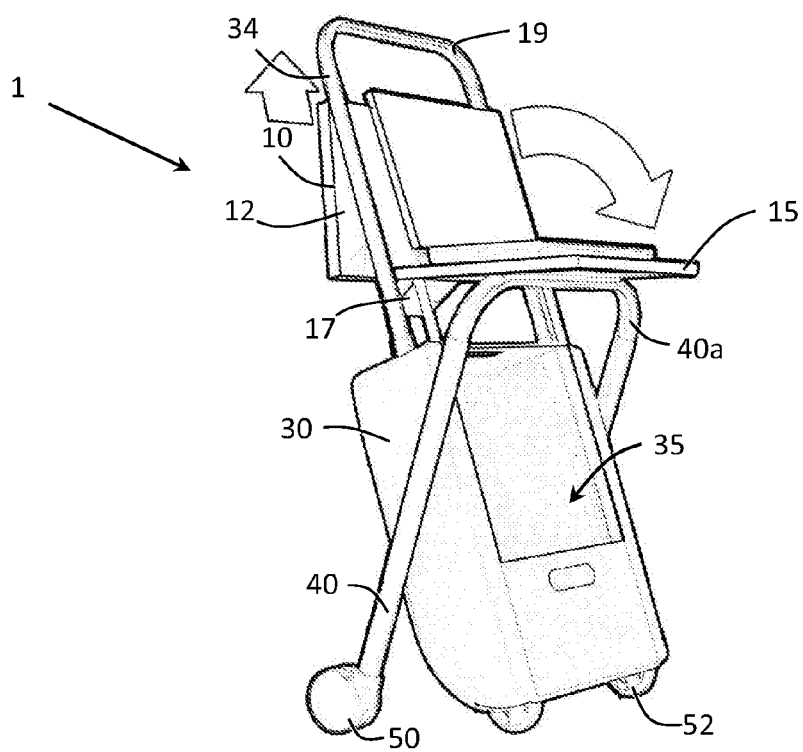

In the illustrated embodiment of FIGS. 3A-3E the interface assembly 10 includes a pull handle 19. Once the cart 1 has been stabilized, the facilitator F may pull on the pull handle 19 to slide the interface assembly 10 from the enclosure 30 through the opening 32 as shown in FIG. 3C. In the illustrated embodiment of FIGS. 3A-3C the tray 15 is embodied as a wall of the enclosure 30 at least in the transporting configuration. Once the interface assembly has been pulled from the enclosure 30, the tray 15 may be pulled up from the enclosure 30 and flipped down or opened away from the interface assembly 10 and be made to rest on the handle portion 40a of the pivoting assembly 40 as shown in FIG. 3D. The assembly 17 may also be flipped down or opened away from the interface assembly 10 to expose the speaker 14, the camera 16 and the microphone 18.

Figure 3E:
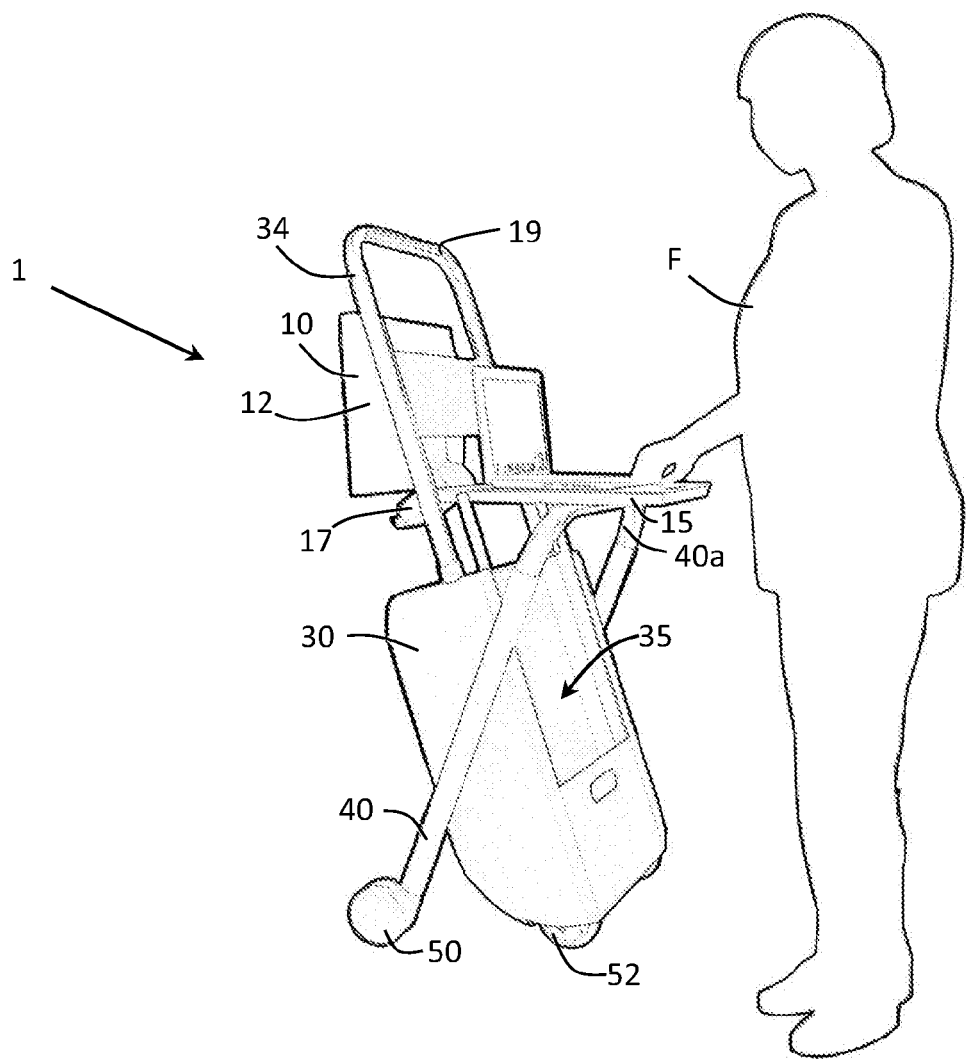
FIG. 3E illustrates the exemplary cart in the deployed configuration.

FIG. 3E illustrates the exemplary cart 1 in the deployed configuration in which the patient (not shown) may interact with the doctor via the interface assembly 10. Also, in the deployed configuration, a facilitator F may monitor various aspects of the communication between doctor and patient by use of the computer 20 which may rest or be attached to the tray 15.

Figure 4A:
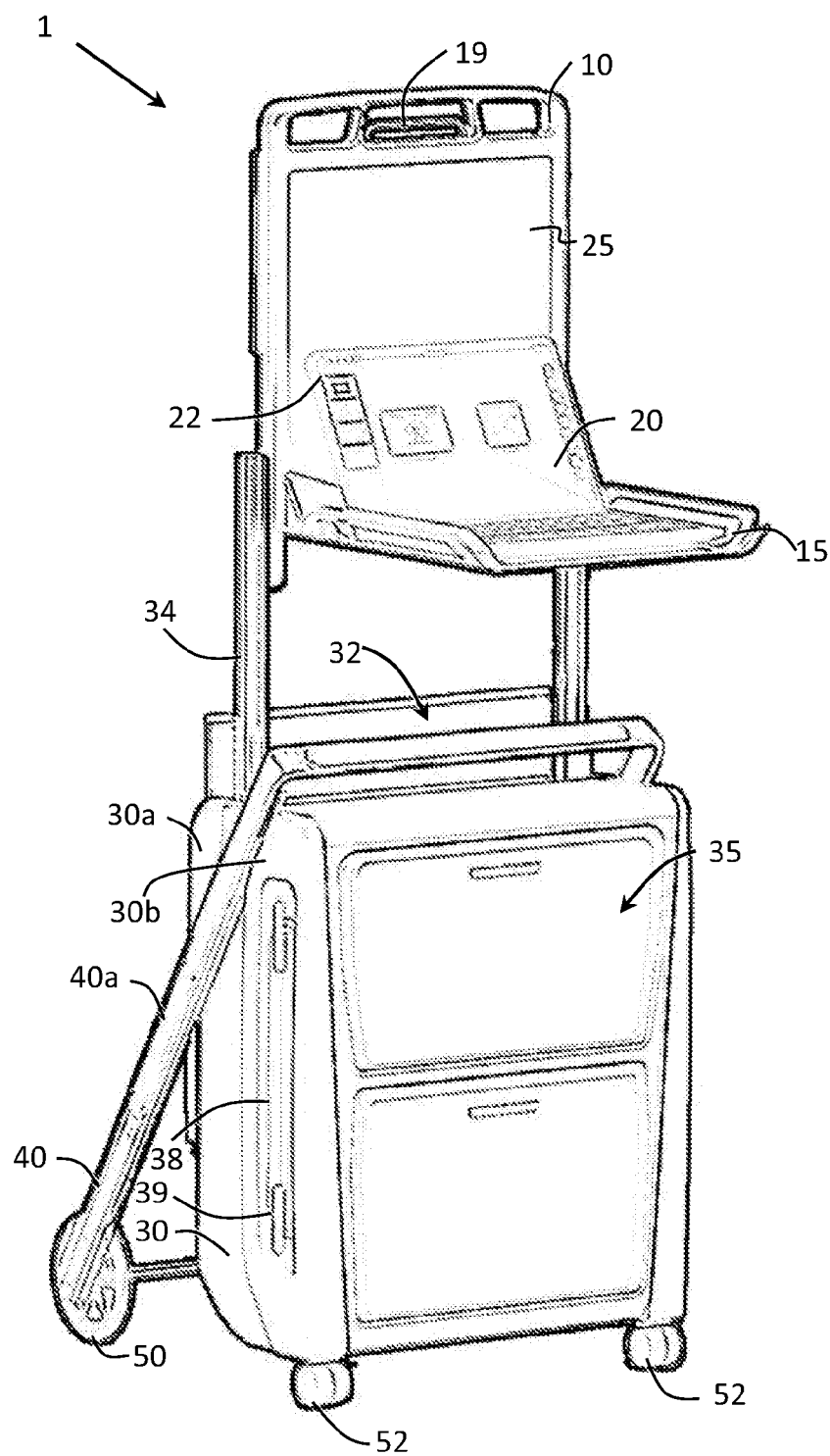
FIGS. 4A and 4B illustrate an additional embodiment of the cart.
Figure 4B:
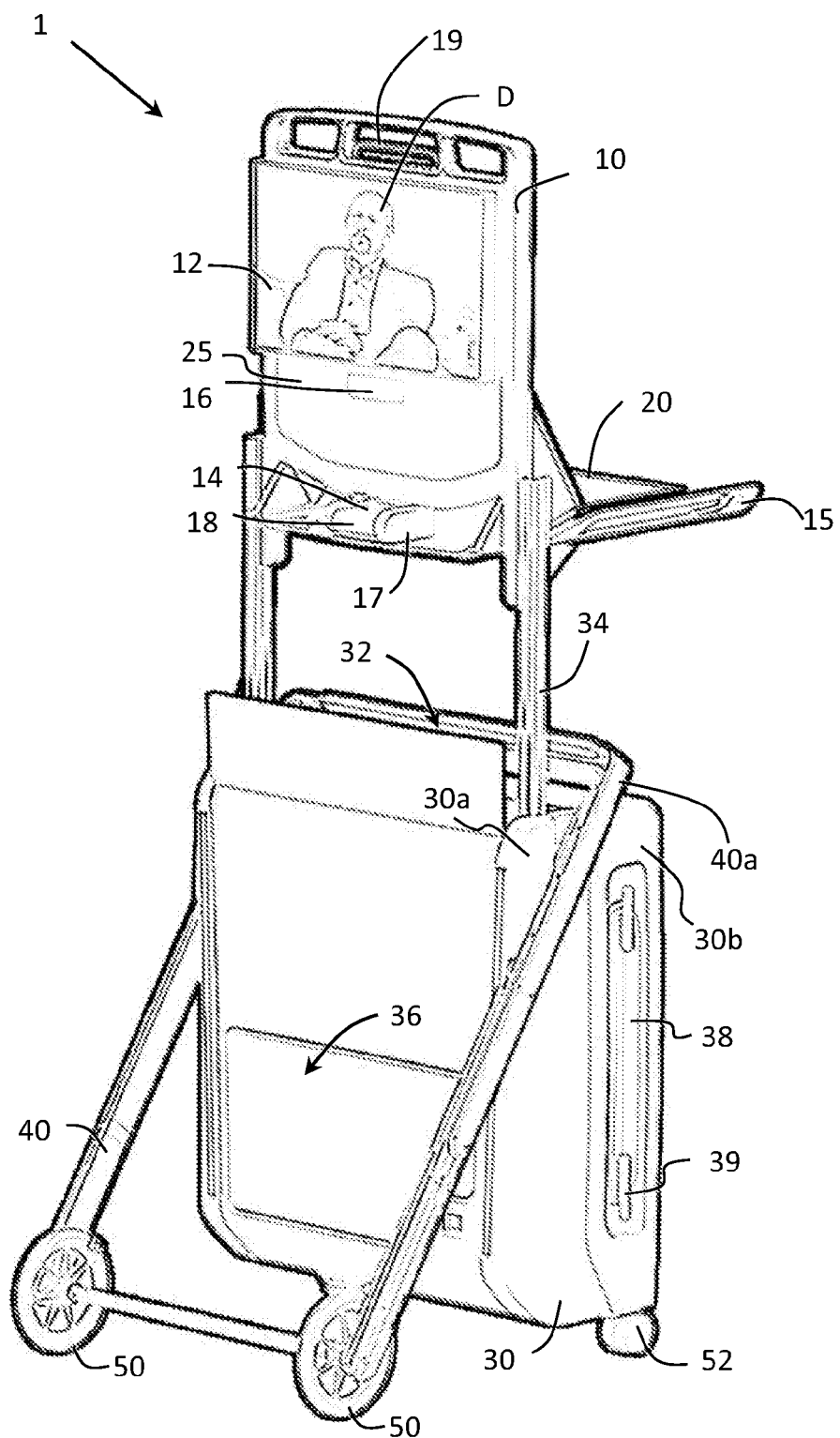

FIGS. 4A and 4B illustrate an additional embodiment of the cart 1. In the illustrated embodiment of FIGS. 4A and 4B the interface assembly 10 includes an alternative design for the tray 15 and the pull handle 19. In the illustrated embodiment, the pull handle 19 may be part of a locking mechanism that locks or unlocks the connecting portion 34 to prevent it or allow it to slide the interface assembly 10 into the enclosure 30 through the opening 32.

The enclosure 30 also has laterally protruding portions 30a and 30b disposed relative to the pivoting assembly 40 such that the pivoting assembly 40 may pivot from the transporting configuration, in which the pivoting assembly engages a first set of walls of the protruding portions 30a and 30b, to the deployed configuration, in which the pivoting assembly 40 engages a second set of walls of the protruding portions 30a and 30b. Engagement of the pivoting assembly 40 and the walls of the protruding portions assists in stabilizing the cart 1.

The cart 1 also includes a battery compartment 36 in which a battery that powers the various components of the cart 1 may be stored. The cart 1 also includes a power cord 38 that may be used to connect to a power outlet to recharge the battery. The cart 1 also includes a power cord reel portion 39 disposed within one of the laterally protruding portions 30a such that in the transporting configuration the power cord 38 is reelable in the power cord reel portion 39 such that the power cord 38 does not interfere with transporting of the cart 1.

In one embodiment, to increase battery life and minimize the weight of the cart 1 among other considerations, the cart 1 includes a main AC-DC converter (not shown) that charges the battery. The various devices of the cart 1 including the first display 12, the speaker 14, the camera 16, the microphone 18, the second display 22 and the computer 20 may operate exclusively off DC power from the battery. This way the cart 1 may include only one main power converter instead of multiple power converters, one for each device. This arrangement reduces power conversion losses and thus increases efficiency and battery life. Additionally, the reduction in the number of power converters also reduces the overall weight of the cart 1.

Figure 5:
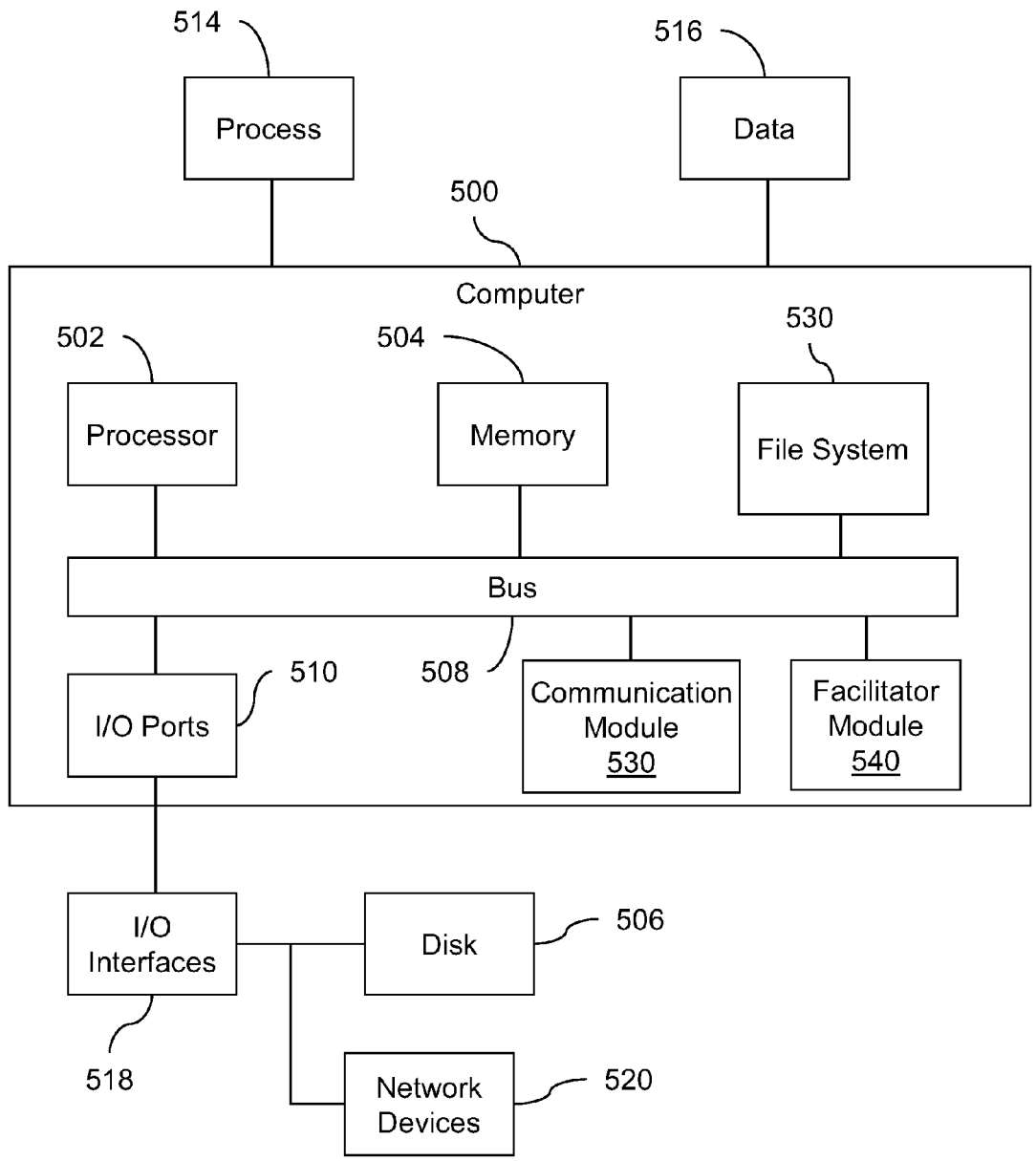
FIG. 5 illustrates a computer environment in which modules related to the exemplary carts may be embodied.

FIG. 5 illustrates a computer 500 that includes a processor 502, a memory 504, and I/O Ports 510 operably connected by a bus 508. In one embodiment, the computer 500 of FIG. 5 corresponds to the computer 20 described above. In another embodiment, the computer 500 of FIG. 5 corresponds to a computer other than the computer 20 described above.

In one example, the computer 500 may include a communication module 530 configured to receive a video and audio communication corresponding to a transmission from a doctor at a location remote from a location of the cart 1 and further configured to cause the video to show on the display 12 and the audio to play through the speaker 14, the doctor/patient communication module further configured to receive a video image from the camera 16 and sound from the microphone 18 and to transmit the video image and the sound to the location remote from the location of the cart 1.

In one example, the computer 500 may include a facilitator module 540 configured to receive the video and audio communication corresponding to the transmission from the doctor and to cause the video to show on the first portion 22a of the second display 22. In another example, the facilitator module 540 may further be configured to receive the video image from the camera 16 and sound from the microphone 18 and to cause the video image to show on the second portion 22b of the second display 22 such that the facilitator may monitor communication between doctor and patient. In yet another example, the facilitator module 540 may further be configured to receive data corresponding to medical forms corresponding to at least one of the doctor or the patient and to show the data corresponding to medical forms on the third portion 22c of the second display 22 such that the facilitator may assist in completing the medical forms.

The processor 502 can be a variety of various processors including dual microprocessor and other multi-processor architectures. The memory 504 can include volatile memory or non-volatile memory. The non-volatile memory can include, but is not limited to, ROM, PROM, EPROM, EEPROM, and the like. Volatile memory can include, for example, RAM, synchronous RAM (SRAM), dynamic RAM (DRAM), synchronous DRAM (SDRAM), double data rate SDRAM (DDR SDRAM), and direct RAM bus RAM (DRRAM).

A disk 506 may be operably connected to the computer 500 via, for example, an I/O Interfaces (e.g., card, device) 518 and an I/O Ports 510. The disk 506 can include, but is not limited to, devices like a magnetic disk drive, a solid state disk drive, a floppy disk drive, a tape drive, a Zip drive, a flash memory card, or a memory stick. Furthermore, the disk 506 can include optical drives like a CD-ROM, a CD recordable drive (CD-R drive), a CD rewriteable drive (CD-RW drive), or a digital video ROM drive (DVD ROM). The memory 504 can store processes 514 or data 516, for example. The disk 506 or memory 504 can store an operating system that controls and allocates resources of the computer 500.

The bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet). The bus 508 can be of a variety of types including, but not limited to, a memory bus or memory controller, a peripheral bus or external bus, a crossbar switch, or a local bus. The local bus can be of varieties including, but not limited to, an industrial standard architecture (ISA) bus, a microchannel architecture (MCA) bus, an extended ISA (EISA) bus, a peripheral component interconnect (PCI) bus, a universal serial (USB) bus, and a small computer systems interface (SCSI) bus.

The computer 500 may interact with input/output devices via I/O Interfaces 518 and I/O Ports 510. Input/output devices can include, but are not limited to, the first display 12, the speaker 14, the camera 16, the microphone 18, the second display 22, a keyboard, a microphone, a pointing and selection device, cameras, video cards, displays, disk 506, network devices 520, and the like. The I/O Ports 510 can include but are not limited to, serial ports, parallel ports, and USB ports.

The computer 500 can operate in a network environment and thus may be connected to network devices 520 via the I/O Interfaces 518, or the I/O Ports 510. Through the network devices 520, the computer 500 may interact with a network. Through the network, the computer 500 may be logically connected to remote computers. The networks with which the computer 500 may interact include, but are not limited to, a local area network (LAN), a wide area network (WAN), and other networks. The network devices 520 can connect to LAN technologies including, but not limited to, fiber distributed data interface (FDDI), copper distributed data interface (CDDI), Ethernet (IEEE 802.3), token ring (IEEE 802.5), wireless computer communication (IEEE 802.11), Bluetooth (IEEE 802.15.1), Zigbee (IEEE 802.15.4) and the like. Similarly, the network devices 520 can connect to WAN technologies including, but not limited to, point to point links, circuit switching networks like integrated services digital networks (ISDN), packet switching networks, and digital subscriber lines (DSL). While individual network types are described, it is to be appreciated that communications via, over, or through a network may include combinations and mixtures of communications.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components. An "operable connection," or a connection by which entities are "operably connected," is one by which the operably connected entities or the operable connection perform its intended purpose. For example, two entities may be "operably connected" to each other directly or through one or more intermediate entities.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (3D. Ed. 1995).

What is claimed is:

1. A cart comprising:
   an enclosure including a connecting portion;
   an interface assembly including a display, a speaker, a camera and a microphone, and operatively connected to the enclosure at least at the connecting portion, the connecting portion operable to reposition the interface assembly from a transporting configuration in which the display, the speaker, the camera and the microphone are disposed inside the enclosure to a deployed configuration in which the display, the speaker, the camera and the microphone are disposed outside of the enclosure;
   a pivoting assembly pivotably disposed in relation to the enclosure; and
   a set of wheels operably connected to at least one of the enclosure or the pivoting assembly, the pivoting assembly operable to pivot from the transporting configuration in which only the set of wheels makes contact with a transporting surface to the deployed configuration in which a portion of the cart in addition to the set of wheels (e.g., a second set of wheels) makes contact with the transporting surface for stabilizing the cart in the deployed configuration.

2. The cart of claim 1, wherein the enclosure has an opening at one end and the connecting portion is operable to reposition the interface assembly from the deployed configuration to the transporting configuration by inserting the interface assembly including the display, the speaker, the camera and the microphone into the enclosure through the opening.

3. The cart of claim 1, comprising:
   a second display operatively connected to the interface assembly and disposed relative to the display of the interface assembly such that in the deployed configuration the second display faces in a direction substantially opposite to a direction to which the display of the interface assembly faces.

* * * * *